United States Patent [19]

Dearling

[11] 4,084,732
[45] Apr. 18, 1978

[54] DIRECT AND INDIRECT FRAGRANCE DISPENSING DEVICE

[76] Inventor: Harry S. Dearling, 25 E. 83rd St., New York, N.Y. 10028

[21] Appl. No.: 727,754

[22] Filed: Sep. 27, 1976

Related U.S. Application Data

[63] Continuation-in-part of Ser. No. 537,923, Jan. 2, 1975, abandoned.

[51] Int. Cl.² ............................................. A61L 9/04
[52] U.S. Cl. ............................. 222/402.17; 239/34; 239/289; 239/326
[58] Field of Search ................... 222/402.17, 321, 331; 239/326, 393, 34, 289, 390

[56] References Cited

U.S. PATENT DOCUMENTS

| | | | |
|---|---|---|---|
| 3,330,481 | 7/1967 | Dearling | 239/326 X |
| 3,940,024 | 2/1976 | Russo et al. | 222/402.17 X |
| 3,972,473 | 8/1976 | Harrison | 239/326 R |

FOREIGN PATENT DOCUMENTS 1,443,314  7/1976  United Kingdom ................... 239/34

*Primary Examiner*—Robert B. Reeves
*Assistant Examiner*—John P. Shannon
*Attorney, Agent, or Firm*—Curtis, Morris & Safford

[57] ABSTRACT

A fragrance dispensing device to provide a fragrance or scent by direct or indirect means comprising a container to discharge a quantity of a suitable fragrance, such as a perfume or deodorizer, and a cover assembly for the container to permit direct discharge in the form of a spray of the fragrance or scent and also to confine the spray discharge within the cover assembly where it is absorbed or adsorbed on a carrier member so that the fragrance or scent may be dissipated in the manner of a sachet.

11 Claims, 4 Drawing Figures

DIRECT AND INDIRECT FRAGRANCE DISPENSING DEVICE

This application is a continuation-in-part of copending application Ser. No. 537,923, filed Jan. 2, 1975, now abandoned.

The present invention relates to a scent or fragrance dispensing device, and more particularly to a scent or fragrance dispensing device that dispenses a measured quantity of a spray fragrance as a vapor spray directly into the air and which may also dispense a fragrance or scent indirectly in the manner of a sachet.

Broadly, the present invention comprises a container adapted to discharge a quantity of a suitable scent or fragrance, such as a perfume or a deodorizer, by either directly discharging a spray mist into the air, by discharging a quantity of the fragrance or spray onto a carrier member capable of absorbing or adsorbing a fragrance sprayed onto it and to dissipate the fragrance or scent in the manner of a sachet or by simultaneously discharging a spray into the air and onto the carrier member. The device utilizes a container to hold the liquid fragrance or scent and the container may be either an aerosol container, wherein the contents are under pressure and are released through a valve as a spray, or the container may include a suitable pump member which when depressed discharges a quantity of the liquid fragrance or scent as a spray. In one embodiment of the present invention, a cover assembly for the container is provided which has two effective positions for dispensing the fragrance or scent. In a first position the spray is released from the container through an appropriate opening as a spray directly into the air and in a second position the spray impinges upon a suitable carrier member which absorbs or adsorbs the fragrance and then slowly dissipates the aroma in the manner of a sachet. In a second embodiment of the present invention the discharge valve is provided with dual outlet ports to simultaneously discharge a spray into the air and to impinge on the carrier member.

Such devices have a number of uses, including particularly to provide an effective room deodorizer where the device can be set to spray an appropriate deodorizing spray directly into the room to dissipate offensive odors. The device may also be used to cause the spray to impinge upon a carrier member which absorbs or adsorbs the deodorizing agent to slowly dissipate a pleasant aroma over a period of time to maintain a pleasant aroma in the room. Another use is for dispensing pharmaceutical preparations, for example decongestents and the like, into a room and then to spray the decongestent onto the carrier member to maintain a beneficial aroma in the room for a long period of time.

It is therefore an object of the present invention to provide a fragrance or deodorizer dispensing device wherein the fragrance or deodorizing agent may be dispensed either as a spray directly into the air or over a longer period of time.

It is a further object of the present invention to provide such a direct and indirect fragrance dispensing device by providing a cover assembly for a container of fragrance which in one position permits direct spray of the fragrance into the air and in another position permits the absorption or adsorption of a quantity of the fragrance onto a carrier member for slower dissipation of the fragrance.

It is a further object of the present invention to provide a fragrance or deodorizer dispensing device which simultaneously dispenses the fragrance or deodorizing agent directly into the air and over a longer period of time.

These and other objects and advantages of the present invention will become more readily apparent after consideration of the following specification and accompanying drawing wherein:

FIG. 5 is an elevational view, partly in section, showing an alternate embodiment of the present invention.

Figure 1:
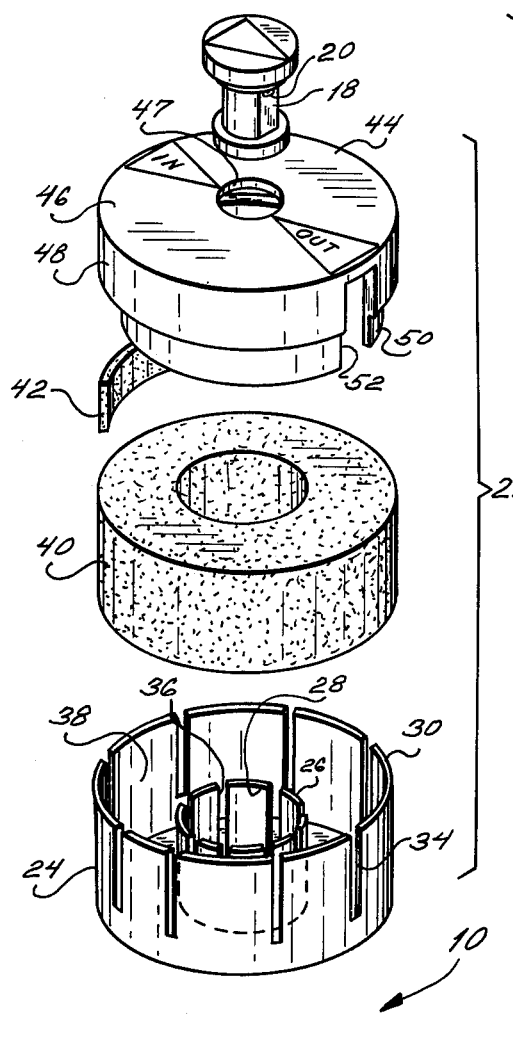
FIG. 1 is an exploded perspective view showing one embodiment of the direct and indirect fragrance dispensing device of the present invention.

With reference to the drawing and particularly FIG. 1, the direct and indirect fragrance or scent dispensing device 10 of the present invention includes a container 12 to hold a quantity of an appropriate fragrance, scent or deodorizer. The container 12 may have any physical shape but preferably, for aesthetic appearances when dispensing a fragrance such as a perfume or pleasant deodorizing scent, a somewhat spherical shape is preferred. Container 12 includes a closure assembly 14 within which is housed a suitable valve (not shown). When the container 12 is of the aerosol type, the valve is a standard aerosol valve member and if the container is not an aerosol container the valve is a suitable valve to operate with an appropriate plunger mechanism when the liquid within container 12 is to be dispensed by pumping. Extending from the closure assembly 14 is a depressable fluid outlet member 16 in the form of a cylindrical segment. Outlet member 16 is in operative communication with the valve in assembly 14 to permit passage of the fragrance through outlet member 16 when member 16 is depressed.

A plunger element 18 (see FIGS. 2 and 3 as well) is provided to frictionally engage the outlet member 16 and plunger member 18 includes a fluid access port therein terminating in a spray outlet 20 to direct the liquid discharged from container 12 in the form of a spray mist. Plunger 18 is adapted to be downwardly depressed and either opens the valve when container 12 is an aerosol to permit passage of the liquid under pressure through outlet member 16 and spray port 20 or, when the container 12 is not an aerosol, plunger element 18 may be repeatedly depressed to discharge liquid from container 12 as a spray mist as well.

Closure assembly 14 and the plunger element 18 are housed within a cover assembly 22 which includes an integral lower housing segment 24 having an inner cylindrical segment 26 provided with a cylindrical opening 28 therethrough joined to an outer cylindrical segment 30 by an annular segment 32. The internal diameter of inner cylindrical segment 28 is large enough to provide a sliding fit over container closure 14 and lower housing 24 rests on the top of the container 12.

A plurality of circumferentially spaced slots 34 are provided within outer cylindrical segment 30 and a plurality of circumferentially spaced slots 36 are provided in interior cylindrical segment 26. The slots 34 and 36 allow for air flow through cover assembly 22 to permit dissipation of the fragrance when the device is used for indirect fragrance dissipation, as will be explained more fully hereinbelow.

Outer cylindrical segment 30, annular member 32 and inner cylindrical segment 26 define an annular storage area 38 to receive a ring shaped segment 40 of an absorbent or adsorbent material. An additional upstanding segment of absorbent or adsorbent material 42 is provided which may be separate from ring 40 or formed integrally therewith. Segment 42 extends around a portion of the periphery of ring 40, for example approximately 90°.

An upper housing 44 is also provided comprising an annular top wall portion 46 having an access opening 47 therethrough and a depending cylindrical wall 48. The lower portion 50 of depending wall 48 is a segment of reduced outer diameter so as to be telescopically engageable within the cylindrical wall segment 30 of the lower housing segment 24. A section of cylindrical wall segment 48 includes a slot 52 formed therein to permit a spray of fragrance or deodorizer from container 12 to be dispelled from the closure assembly.

The carrier member 42 is disposed within lower housing segment 24 with upstanding segment 42 positioned diametrically opposite spray access slot 52. The plunger member 18 is rotatably disposed about container outlet port 16 through access opening 47 so that the spray access port 20 may be oriented to point either towards spray access slot 52 in top cover 44 or toward carrier member segment 42.

Figures 2, 3:
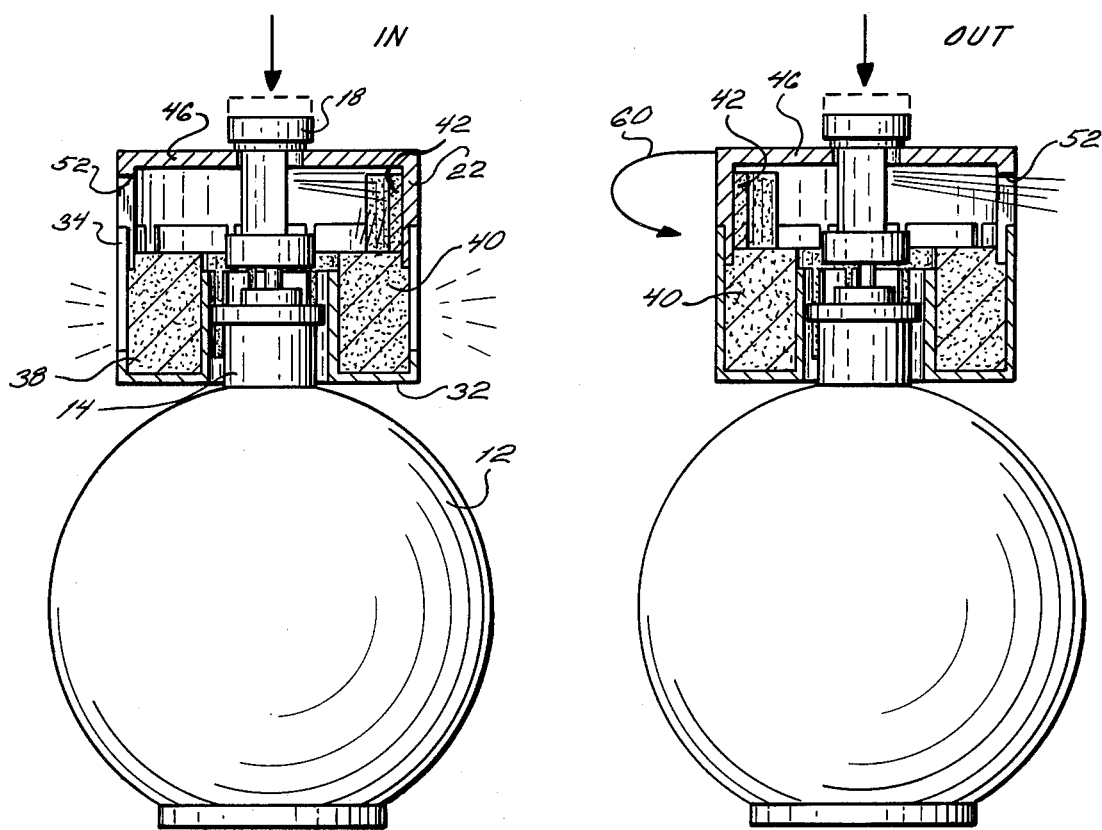
FIG. 2 is an elevational view, partly in section, showing one embodiment of the fragrance dispensing device of the present invention in its indirect fragrance dispensing orientation.
FIG. 3 is a view similar to FIG. 2 showing the fragrance dispensing device of the present invention in its direct fragrance dispensing orientation.

Thus, when plunger 18 is oriented in the position shown in FIG. 2 and is depressed, the spray dispelled from container 12 impinges upon carrier segment 42 and is absorbed or adsorbed thereon and is in turn imparted to carrier member segment 40. When this occurs, the aroma or scent from the fragrance or deodorant remains impregnated on the carrier members 40 and 42 and is slowly dissipated by air flowing through slots 34 and 36 until that quantity of spray expelled from container 12 has completely dried and lost all semblance of aroma. Thus, the aroma scent is allowed to permeate through the room in which the container 12 is placed for a considerable period of time.

When plunger 18 is oriented so that spray access port 20 is in register with spray access slot 52 in the top cover member and plunger 18 is depressed, the spray of fragrance or scent expelled from container 12 is allowed to pass freely through the container housing without impinging upon the carrier member within and is dispelled in a room in which container 12 is used in the form of a spray or mist.

Figure 4:
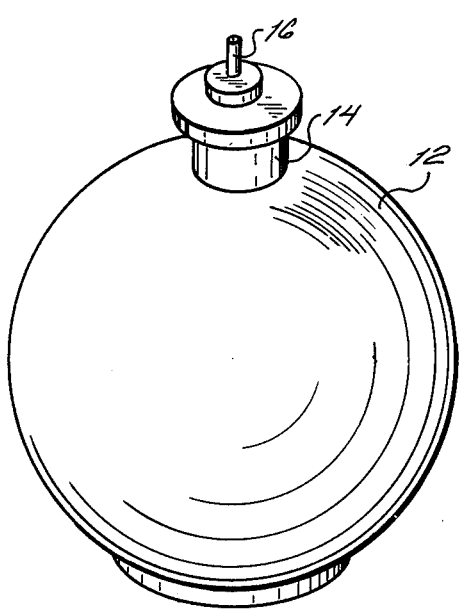
FIG. 4 is a top plan view of the fragrance dispensing device of the present invention.
Figure 4:
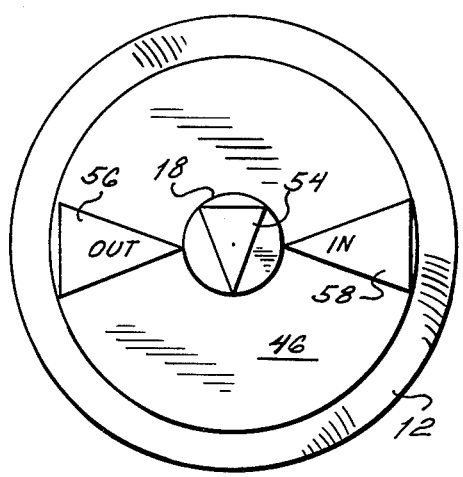

Reference is now made to FIG. 4, where it is seen that the top of plunger 18 includes a scribed indicia 54 thereon in the form of an arrowhead and indicia 56, with the phrase "out", and indicia 58, with the phrase "in", are scribed on the exterior surface of top wall 46. The indicia 56 is disposed over spray access slot 52 so that when arrowhead 54 points to indicia 56 the spray access port 20 is oriented to dispel the spray out slot 52. Similarly, when arrowhead 54 is pointed toward indicia 58, the spray impinges upon the carrier member within cover assembly 22.

While the present invention has been described as having plunger member 18 rotatably mounted it is apparent that plunger member 18 can be secured to be non-rotatable and the cover assembly 22 made to be rotatable, as indicated by the arrow 60 in FIG. 3, to select direct or indirect fragrance dispensing.

In an alternate embodiment of the present invention provision is made to simultaneously direct the fragrance or scent directly into the air and onto the carrier member where it is absorbed or adsorbed so as to dissipate the fragrance over a longer period of time.

In this embodiment, shown in FIG. 5, like elements are numbered the same as in the embodiment of FIGS. 1–4. In this alternate embodiment the plunger element 18 includes diametrically opposed spray outlets 60 and 62 so that when plunger 18 is actuated the spray is directed out both spray outlets 60 and 62 in diametrically opposed directions.

With this construction, actuation of plunger 18 simultaneously directs spray out slot 52 into the air and onto carrier segment 42 where it is absorbed or adsorbed and in turn imparted to the carrier segment 40.

Thus spray is discharged directly into the air and also imparted to the carrier segments where the fragrance may be slowly dissipated over a longer period of time by air flowing through slots 34 and 36 in the same manner as in the embodiment of FIGS. 1–4.

Thus the present invention provides a relatively simple and economically feasible construction to permit dual fragrance dispensing either by directly spraying a mist of fragrance or scent and also by indirect fragrance dispensing to permeate the aroma more slowly or by simultaneous direct and indirect spray.

What is claimed is:

1. A fragrance dispensing device for direct or indirect dissemination of a fragrance comprising:
   a cover assembly including a cover member adapted to be positioned over the discharge outlet means of a fragrance container,
   said cover assembly including a housing adapted to hold a carrier member to receive said fragrance whereby said fragrance may be dissipated over a period of time,
   means in said cover member to provide an access passage from within said cover member to the exterior of said cover member,
   actuation means including a fragrance spray outlet port therein within said cover assembly and cooperable with said discharge outlet means to discharge a spray of said fragrance from said outlet port, and
   said actuation means and cover assembly being movable relative to each other between a first position wherein said outlet port is oriented in register with said access passage in said cover assembly to discharge said fragrance directly to the exterior of said cover member as a spray and a second position wherein said outlet port is oriented to discharge said fragrance onto said carrier member within said cover assembly to disseminate said fragrance indirectly.

2. A fragrance dispensing device as defined in claim 1 wherein said cover assembly comprises an interior wall segment defining an opening therethrough adapted to receive said discharge outlet means of said fragrance container and an exterior wall segment spaced from said interior wall segment and interconnected to said interior wall segment to define a storage area to accommodate said carrier member.

3. A fragrance dispensing device as defined in claim 2 wherein said actuation means comprises a plunger member disposed within said opening defined by said interior wall segment and said actuation means is rotatably mounted on said discharge outlet means of said fragrance container thereby to be rotatable between said first and second positions to select direct and indirect dissemination of said fragrance.

4. A fragrance dispensing device as defined in claim 2 wherein said actuation means comprises a plunger member disposed within said opening defined by said interior wall segment and said actuation means is fixed with its spray outlet port oriented in one direction and said cover assembly is rotatably disposed about said fragrance container thereby to be rotatable between said first and second positions to select direct and indirect dissemination of said fragrance.

5. A fragrance dispensing device as defined in claim 1 wherein said cover assembly comprises a top wall, a bottom wall and a wall segment interconnecting said top and bottom wall about the peripheral extent to said top and bottom walls to define a storage area therein, said interconnecting wall segment provided with said access passage therethrough.

6. A fragrance dispensing device as defined in claim 5 wherein said carrier member is disposed in said storage area and said interconnecting wall segment includes a plurality of spaced slots therethrough to provide means for air flow through said cover assembly to permit dissemination of said fragrance when said carrier member is impregnated with said fragrance.

7. A fragrance dispensing device for direct and indirect dissemination of a fragrance comprising:
   a cover assembly including a cover member adapted to be positioned over the discharge outlet means of a fragrance container,
   said cover assembly including a housing adapted to hold a carrier member to receive said fragrance whereby said fragrance may be dissipated over a period of time,
   means in said cover member to provide an access passage from within said cover member to the exterior of said cover member,
   actuation means including a fragrance spray outlet port therein within said cover assembly and cooperable with said discharge outlet means to discharge a spray of said fragrance from said outlet port, and
   said actuation means comprising at least a pair of spray outlet ports disposed on diametrically opposite sides with one of said spray outlet ports oriented in register with said access passage in said cover assembly to discharge said fragrance directly to the exterior of said cover member as a spray and the other of said spray outlet ports oriented to simultaneously discharge said fragrance onto said carrier member within said cover assembly to disseminate said fragrance indirectly.

8. A fragrance dispensing device as defined in claim 7 wherein said cover assembly comprises an interior wall segment defining an opening therethrough adapted to receive said discharge outlet means of said fragrance container and an exterior wall segment spaced from said interior wall segment and interconnected to said interior wall segment to define a storage area to accommodate said carrier member.

9. A fragrance dispensing device as defined in claim 8 wherein said actuation means comprises a plunger member disposed within said opening defined by said interior wall segment and said spray outlet ports are disposed on diametrically opposed positions on said plunger.

10. A fragrance dispensing device as defined in claim 7 wherein said cover assembly comprises a top wall, a bottom wall and a wall segment interconnecting said top and bottom wall about the peripheral extent of said top and bottom walls to define a storage area therein, said interconnecting wall segment provided with said access passage therethrough.

11. A fragrance dispensing device as defined in claim 10 wherein said carrier member is disposed in said storage area and said interconnecting wall segment includes a plurality of spaced slots therethrough to provide means for air flow through said cover assembly to permit dissemination of said fragrance when said carrier member is impregnated with said fragrance.

* * * * *